United States Patent [19]

Mueller et al.

[11] 4,224,251
[45] Sep. 23, 1980

[54] PREPARATION OF 5-DIETHYLAMINOPENTAN-2-OL

[75] Inventors: Herbert Mueller; Herbert Toussaint, both of Frankenthal; Arnold Wittwer, Ludwigshafen, all of Fed. Rep. of Germany

[73] Assignee: BASF Aktiengesellschaft, Fed. Rep. of Germany

[21] Appl. No.: 57,085

[22] Filed: Jul. 12, 1979

[30] Foreign Application Priority Data

Aug. 23, 1978 [DE] Fed. Rep. of Germany ....... 2836831

[51] Int. Cl.$^2$ .............................................. C07C 85/24
[52] U.S. Cl. .................. 260/584 R; 260/690

[58] Field of Search ....................... 260/584 R, 583 H; 252/473, 474

[56] References Cited

FOREIGN PATENT DOCUMENTS 2536273 2/1977 Fed. Rep. of Germany ...... 260/584 R

Primary Examiner—John Doll
Attorney, Agent, or Firm—Keil & Witherspoon

[57] ABSTRACT

5-Diethylaminopentan-2-ol is obtained from 1-diethylamino-pent-2-yn-4-ol by hydrogenation, if a nickel catalyst is used in the presence of a basic alkali metal compound or alkaline earth metal compound and the hydrogenation is carried out in the absence of water.

4 Claims, No Drawings

PREPARATION OF 5-DIETHYLAMINOPENTAN-2-OL

5-Diethylaminopentan-2-ol, an important intermediate for organic syntheses, especially in the pharmaceutical sector, is prepared industrially by hydrogenating 1-diethylaminopent-2-yn-4-ol. In this reaction it is important that the triple bond should be completely hydrogenated. Acetylenic or olefinic impurities which may remain if the catalysts used are not very active result, for example, in unacceptable contamination of the end product, from which they can only be removed with difficulty.

The conventional powerful hydrogenating catalysts, eg. platinum, palladium, Raney nickel and the like, which are employed for hydrogenating carbon-carbon double bonds, are also used for hydrogenating triple bonds to paraffinic bonds. However, when hydrogenating the diethylaminopentynol it is found that it is particularly the very active platinum, palladium, nickel and copper catalysts which lead to a side reaction whereby diethylamine or water is eliminated from the starting material, resulting in aminopentan-2-ol and diethylaminopentane, respectively. Since the acetylenically unsaturated starting compound is relatively valuable, these side reactions are undesirable, especially for economic reasons, but also cause technical problems because the products of the side reactions must be separated off.

It is an object of the present invention to provide a process for the preparation of 5-diethylaminopentan-2-ol by catalytically hydrogenating 1-diethylaminopent-2-yn-4-ol, whereby the formation of pentan-2-ol and diethylaminopentane can be suppressed and complete reduction can be achieved. We have found that this object is achieved by using, as the hydrogenating catalyst, nickel together with a basic alkali metal or alkaline earth metal compound and substantially excluding water.

In practice, excluding water means, for the purposes of the invention, that the water content in the reaction mixture is kept low, preferably lower than 2 percent by weight. Basically, the lower the water content in the reaction mixture, the more specific is the reaction.

In general, the particular mixture of starting material and end product serves as the solvent, ie. extraneous solvents are not necessary.

Particularly suitable basic compounds are the oxides and hydroxides of the alkali metals and alkaline earth metals, and their carbonates and bicarbonates. Specific examples are sodium hydroxide, potassium oxide, calcium hydroxide, lithium hydroxide, barium hydroxide, strontium hydroxide, sodium carbonate, sodium bicarbonate and sodium acetate. As a rule, these compounds are admittedly water-soluble, but insoluble or only sparingly soluble in the reaction mixture. Calcium carbonate is less active.

The active amount of these compounds is in general from 0.02 to 2% by weight, based on the amount of reaction mixture, but it can also, without disadvantage, be higher.

A particularly suitable catalyst is Raney nickel. In carrying out the hydrogenation, catalytic amounts, ie. very low amounts, of Raney nickel suffice. In general, a catalyst concentration of from 0.5 to 5% is used. A sufficient rate of reaction is achieved with as little as 1% of Raney nickel. Other suitable nickel catalysts are for the most part commercially available catalysts which contain nickel on a carrier, eg. silica gel, alumina or pumice. The reaction can be carried out with the catalyst in suspension or in a fixed bed, depending on the form of the catalyst. Of course, the above data regarding the amounts of catalyst only apply to the case of suspended catalysts.

The reaction takes place sufficiently rapidly even at room temperature and atmospheric pressure. Since the reaction is strongly exothermic, it is in general carried out at from 50° to 100° C., to provide a sufficient temperature difference for effective heat removal. In this range, the reaction temperature has no influence on the selectivity of the reaction; temperatures above 150° C. should however be avoided. The hydrogen pressure employed is not critical. The hydrogenation takes place at high speed even at hydrogen partial pressures of less than 1 bar. Hence, the use of pressures above 10 bar is in general avoided, if only for cost reasons.

EXAMPLE

A pressure kettle having a useful volume of 2,000 ml and equipped with a high-speed stirrer is charged successively with 1,000 g of diethylaminopentynol (containing about 0.3% of water), 20 g of Raney nickel (containing 35% of water) and 1.2 g of sodium hydroxide powder (about 98% pure). At a hydrogen pressure of 5 bar and an initial temperature of 19° C., a vigorous reaction commences immediately and after 10 minutes 50° C. is reached. The reaction is then continued at the latter temperature, which is maintained by cooling. After about 70 minutes, the exothermic effect subsides; the reaction mixture is now kept at 50° C. by heating, until the calculated amount of hydrogen has been taken up, which requires 5 hours. The mixture is allowed to settle and cool. The supernatant clear solution is syphoned off. A sample distillation at 1 mbar and 190° C. shows that the reaction product contains less than 0.2% of non-volatile constituents. Its composition in percent by weight, according to analysis by gas chromatography, is shown in the Table which follows. A further 4 experiments are carried out with the catalyst which has remained in the kettle, and the results of these are also shown in the Table.

TABLE

| Experiment | 1 | 2 | 3 | 4 | 5 |
|---|---|---|---|---|---|
| Diethylamine | 0.5 | 0.2 | 0.1 | 0.1 | 0.4 |
| Pentan-2-ol | 0.3 | 0.2 | 0.3 | 0.5 | 0.3 |
| Diethylaminopentane | 1.0 | 0.1 | 0.2 | 0.3 | 0.2 |
| Diethylaminopentanol | 94 | 98 | 98 | 98 | 98 |
| Diethylaminopentenol | 0.1 | — | — | — | — |
| Diethylaminopentynol | 0.1 | — | — | — | — |
| Unknown compounds | 3 | 1 | 1 | 0.9 | 0.9 |
| Water | 1 | 0.5 | 0.4 | 0.2 | 0.2 |

COMPARATIVE EXPERIMENT

The above procedure is followed, except that no sodium hydroxide powder is added. The reaction mixture obtained comprises 70% of diethylaminopentanol, about 10% of diethylamine, 10% of pentan-2-ol and 10% of diethylaminopentane.

MODIFIED EXAMPLES

The yield of diethylaminopentanol is of the same order of magnitude as described in the Example, ie. from 97 to 98%, if, for example, 1.5 g of 50% strength potassium hydroxide solution are used instead of sodium hydroxide. A yield of about 93% is obtained with lithium hydroxide or calcium hydroxide as the added base. A yield of from 88 to 89% is observed if sodium hydroxide is replaced by sodium carbonate or sodium bicarbonate.

A catalyst which according to analysis consisted of 58% of nickel oxide, 15% of magnesium oxide, 24% of $SiO_2$, 1% of $Cr_2O_3$ and 2% of $Na_2CO_3$ and was reduced at 350°–400° C. before being used gave equally good results to those obtained with Raney nickel and sodium hydroxide powder. This catalyst had been prepared by impregnating a commercial catalyst, containing nickel on a magnesium silicate carrier, with concentrated sodium carbonate solution until 2% by weight of $Na_2CO_3$ had been taken up, and drying the product under reduced pressure. If this catalyst is used without first subjecting it to the treatment with sodium carbonate, the desired product is obtained in about 15% lower yield.

The use of alkali metal compounds or alkaline earth metal compounds which normally also show basic behavior but which are regarded as completely insoluble in water, for example calcium carbonate or barium carbonate, offers virtually no advantage.

We claim:

1. A process for the preparation of 5-diethylaminopentan-2-ol by catalytically hydrogenating 1-diethylaminopent-2-yn-4-ol, wherein the catalyst used is nickel in the presence of an effective amount of a basic alkali metal compound or alkaline earth metal compound, and water is substantially excluded.

2. A process as claimed in claim 1, wherein the reaction is started at room temperature and the reaction temperature is kept below 100° C.

3. A process as claimed in claim 1, wherein hydrogenation is carried out under a hydrogen pressure of less than 10 bar.

4. A process as claimed in claim 1, wherein the water content in the reaction mixture is kept at below 2%.

* * * * *